United States Patent [19]

Cragoe, Jr.

[11] Patent Number: 4,675,341

[45] Date of Patent: Jun. 23, 1987

[54] [(5,6-DICHLORO-3-OXO-9A-PROPYL-2,3,9,9A-TETRAHYDROFLUOREN-7-YL)OXY]ETHANOL AND ITS DERIVATIVES

[75] Inventor: Edward J. Cragoe, Jr., Lansdale, Pa.

[73] Assignee: Merck & Co., Inc., Rahway, N.J.

[21] Appl. No.: 896,022

[22] Filed: Aug. 13, 1986

[51] Int. Cl.$^4$ .................... C07C 101/18; C07C 69/60; C07C 69/40; A61K 31/22

[52] U.S. Cl. .................................. 514/548; 514/551; 514/684; 560/173; 560/194; 568/326

[58] Field of Search ................ 560/173, 194; 568/326; 514/548, 551, 684

[56] References Cited

U.S. PATENT DOCUMENTS

| | | | |
|---|---|---|---|
| 4,316,043 | 2/1982 | Cragoe | 562/461 |
| 4,317,922 | 3/1982 | Cragoe | 562/461 |
| 4,337,354 | 6/1982 | Cragoe | 562/461 |
| 4,356,313 | 10/1982 | Cragoe | 562/461 |
| 4,356,314 | 10/1982 | Cragoe | 562/461 |

*Primary Examiner*—Michael L. Shippen
*Attorney, Agent, or Firm*—Charles M. Caruso; Hesna J. Pfeiffer

[57] ABSTRACT

The invention relates to novel [(5,6-dichloro-3-oxo-9a-propyl-2,3,9,9a-tetrahydrofluoren-7-yl)oxy]ethanol, its derivatives, and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections including that due to AIDS virus, various brain concussions and elevated intracranial pressure.

9 Claims, No Drawings

[(5,6-DICHLORO-3-OXO-9A-PROPYL-2,3,9,9A-TETRAHYDROFLUOREN-7-YL)OXY]ETHANOL AND ITS DERIVATIVES

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

Recent publications entitled "Agents for the Treatment of Brain Injury" 1. (Aryloxy)alkanoic Acids, Cragoe et al, J. Med. Chem., (1982) 25, 567–569, and "Agents for the Treatment of Brain Edema: ,2[(2,3,9,9a-tetrahydro-3-oxo-9substituted-1H-fluoren-7-yl)oxy] Alkanoic Acids and Some of Their Analogs", Cragoe et al., J. Med. Chem. (1986), 29, 825–841, report on recent experimental testing of agents for treatment of brain injury and review the current status of treatment of brain injury. Additionally, U.S. Pat. Nos. 4,316,043, 4,317,922, 4,337,354, 4,356,313 and 4,356,314 disclose certain alkanoic and cycloalkanoic acids for the treatment of grey matter edema.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

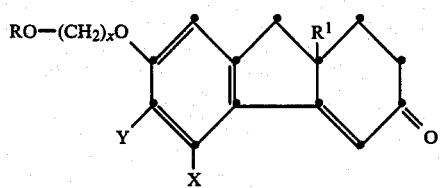

wherein:

R is H, $-\overset{O}{\underset{\|}{C}}(CH_2)_yN(CH_3)_2$,

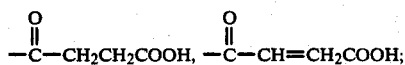

$R^1$ is lower alkyl, branched or unbranched, containing from 1 to 5 carbon atoms such as methyl, ethyl, n-propyl, isopropyl and the like, aryl such as phenyl, halo substituted aryl such as p-fluorophenyl, o-fluorophenyl, p-chlorophenyl and the like, aralkyl such as benzyl, cycloalkyl containing from 3 to 6 nuclear carbon atoms such as cyclopropyl, cyclobutyl, cyclopentyl and the like, or cycloalkyl-lower alkyl containing from 4 to 7 total carbon atoms such as cyclopentylmethyl and the like;

X and Y are halo or lower alkyl, such as methyl;

x is 1 to 4; and y is 1 to 3.

Since the 9acarbon atom in the molecule is asymmetric, the compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Likewise, since certain products of the invention are acidic, the invention also includes the obvious pharmaceutically acceptable salts such as the sodium, potassium, ammonium, trimethylammonium, piperazinium, 1-methylpiperazinium, guanidinium, bis(2-hydroxyethyl)ammonium, N-methyl-glucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.)in vacuo.

Although the invention primarily involves novel [(5,6-dichloro-3-oxo-9-apropyl-2,3,9,9a-tetra hydrofluoren-7-yl)oxy]ethanol and their salts, it also includes their derivatives, such as oximes, hydrazones and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II

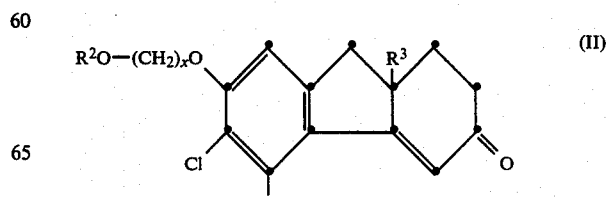

wherein:

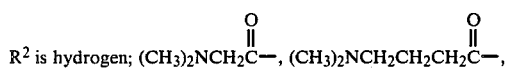

R[2] is hydrogen; $(CH_3)_2NCH_2\overset{O}{\underset{\|}{C}}-$, $(CH_3)_2NCH_2CH_2CH_2\overset{O}{\underset{\|}{C}}-$,

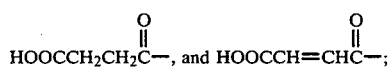

$HOOCCH_2CH_2\overset{O}{\underset{\|}{C}}-$, and $HOOCCH=CH\overset{O}{\underset{\|}{C}}-$;

R[3] is lower alkyl, branched or unbranched, containing from 1 to 5 carbon atoms; and x is 1 or 2.

Also included are the enantiomers of each racemate.

A preferred compound is R(+) [(5,6-dichloro1,2,9-,9a-tetrahydro-9a-propyl-1H-fluoren-7-yl)oxy]ethanol.

Also preferred is R(+) [(5,6-dichloro-1,2,9,9a-tetrahydro-9a-propyl-1H-fluoren-7-yl)oxy]ethyl 4-(dimethylamino)butyrate hydrochloride.

Also preferred is R(+) [(5,6-dichloro-1,2,9,9a-tetrahydro-9a-propy-1H-fluoren-7-yl)oxy]ethyl (dimethylamino)acetate hydrochloride Also preferred is R(+) [(5,6-dichloro-1,2,9,9a-tetrahydro-9a-propy-1H-fluoren-7-yl)oxy]ethyl 3-carboxypropionate.

Also preferred is R(+) [(5,6-dichloro-1,2,9,9a-tetrahydro-9a-propyl- 1H-fluoren-7-yl)oxy]ethyl 3-carboxyacrylate.

Especially preferred are the pure enantiomers since, in most instances, one enantiomer is more active biologically then its antipode.

Included within the scope of this invention are the pharmaceutically acceptable salts of basic or acidic esters of [(5,6-dichloro-3-oxo-9a-propyl-2,3,9,9a-tetrahydrofluoren-7-yl)oxy]ethanol (Ib) and its derivatives since a major medical use of these compounds is solutions of their soluble salts which can be administered parenterally.

Thus, the acid addition salts can be prepared by the reaction of the acidic esters of [(5,6-dichloro-3-oxo-9a-propyl-2,3,9,9a -tetrahydrofluoren-7-yl)oxy]ethanol and its derivatives with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methylpiperazine, guanidine, bis-(2-hydroxyethyl)amine, N-methylglucosamine and the like salts. The salts of the basic esters of this invention may be prepared by reaction with an appropriate pharmaceutically acceptable mineral acid or organic carboxylic acid, such as hydrochloric acid, sulfuric acid, hydrobromic acid, isethionic acid, methanesulfonic acid, maleic acid, succinic acid, acetic acid and the like. The salts selected are derived from among the nontoxic, pharmaceutically acceptable acids.

The compounds of this invention, such as:

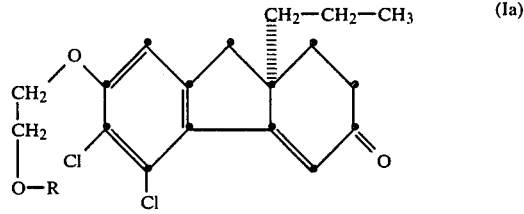

where R = H(Ib), $-\overset{O}{\underset{\|}{C}}-(CH_2)_yN(CH_3)_2(Ic)$,

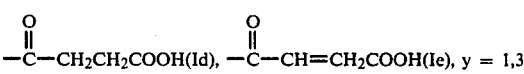

$-\overset{O}{\underset{\|}{C}}-CH_2CH_2COOH(Id)$, $-\overset{O}{\underset{\|}{C}}-CH=CH_2COOH(Ie)$, y = 1,3

The compounds of Formula I can serve as prodrugs of the corresponding carboxylic acids of Formula IIIa known to be agents for the treatment of brain injury (see U.S. Pat. Nos. 4,316,043 4,317,922, 4,337,354, 4,356,313, 4,356,314).

I 

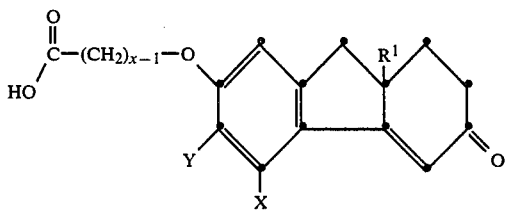

(IIIa)

Compound IIIa is obtained from compound I by well-known metabolic processes. Thus, when R=H, an oxidative metabolism occurs and when R= other than H a hydrolytic and oxidative metabolism occurs to produce IIIa.

Since it is convenient to administer the compounds parenterally, particularly intravenously, it is convenient to make a derivative of Ib which can be converted to a watersoluble salt. Thus, with the compound where

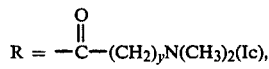

$R = -\overset{O}{\underset{\|}{C}}-(CH_2)_yN(CH_3)_2(Ic)$, a salt can be formed from a organic or inorganic acid which is water soluble. Likewise, with the compound where

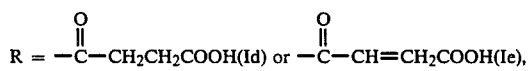

$R = -\overset{O}{\underset{\|}{C}}-CH_2CH_2COOH(Id)$ or $-\overset{O}{\underset{\|}{C}}-CH=CH_2COOH(Ie)$, a salt can be formed from an organic or inorganic base which is water soluble.

The compounds of this invention are prepared as follows:

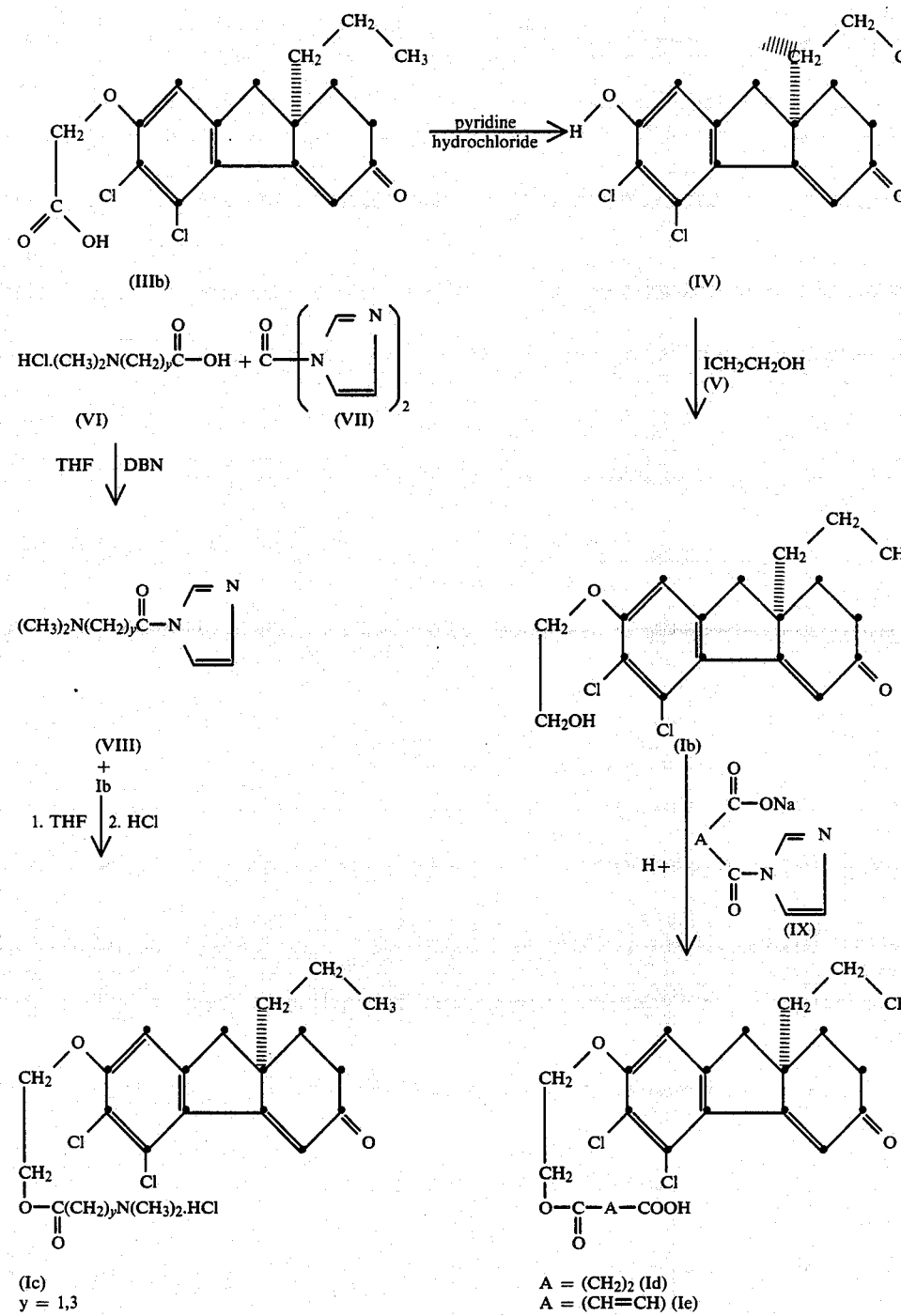

Phenol IV is prepared from pure III by heating with molten pyridine hydrochloride. The reaction is generally carried out using 25 to 35 moles of pyridine hydrochloride to one of III. The stirring mixture is heated preferably at 190° C. for 15 minutes. Somewhat longer periods are required at lower temperatures. However, excess heating leads to excessive decomposition products.

Reaction of compound IV with 2-iodoethanol (V) in a solvent such as acetone in the presence of a base such as potassium carbonate leads to compound Ib. It is convenient to heat the reaction mixture at the reflux temperature of acetone for periods of 18–36 hours to complete the reaction. Other solvents such as 2-butanone or dimethylformamide can be used, however, the temperature of the reaction should be kept in the range of 50°–60° C. Other bases such as sodium carbonate may be used.

The reaction of compounds Ib with compound VIII leads to the formation of compound (Ic). Compound VIII is formed by the reaction of compound VI with carbonyldiimidazole (VII) in the presence of a base such as 1,5-diazabicyclo[4.3.0]nonane (DBN) or 1,-diazabicyclo[5.4.0]undecane (DBU) in a solvent such as tetrahydrofuran (THF) or dioxane. The reaction is completed in 1 to 5 hours.

The addition of compound Ib to a preformed solution of VIII in THF and stirring the mixture at a temperature of 20° to 35° C. for 12 to 16 hours leads to the formation of the desired product. Acidification of Ib with an acid such as hydrochloric acid leads to the formation of compound Ib in the form of its hydrochloride salt.

The reaction of compound Ib with compound IX upon acidification produces compound Id if A=—(CH$_2$)$_2$—and compound Ie if A=—CH=CH—. Compound IX is prepared from either succinic acid or maleic acid (1 mole) by treatment with imidazole sodium followed by reaction with carbonyldiimidazole (VII) (1 mole). The reaction is carried out in the presence of dimethylformamide and the reaction is complete at ambient temperature within about 15 to 30 minutes. Compound Ib is added to the reaction mixture along with a catalytic amount of sodium methoxide (CH$_3$ONa) (0.05 mole equivalent). The product (compound Id or Ie) is isolated by evaporation of the solvent, adding water and acidification of the solution with hydrochloric acid.

It is to be noted that the compounds described above consist of the pure R-enantomer since they are derived from compound IIIb, which is a pure R-enantiomer.

It is to be recognized that these compounds of Formula I possess an asymmetric carbon atom at position 9a and, therefore, consist of racemates composed of two enantiomers. However, an appropriate intermediate phenol (i.e. Compound IV) which consists of one pure enantiomer, permits the synthesis of pure enantiomeric products of Formula I.

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions and elevated intracranial pressure, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glasgow Coma Score or similar scoring system. Such a scoring system is often valuable in selecting the patients who are candidates for therapy of this kind.

The compounds of this invention can be administered by a variety of established methods, including intravenously, intramuscularly, subcutaneously, intracisternally or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.01 mg/kg to 20 mg/kg of body weight as a single dose, preferably from 0.05 mg/kg to 10 mg/kg. An alternative to the single dose schedule is to administer a primary loading dose followed by a sustaining dose of half to equal the primary dose, every 4 to 24 hours. When this multiple dose schedule is used, the dosage range may be higher than that of the single dose method. Another alternative is to administer an ascending dose sequence of an initial dose followed by a sustaining dose of 1.5 to 2 times the initial dose every 4 to 24 hours. For example, 3 intravenous doses of 4, 6 and 8 mg/kg of body weight can be given at 6 hour intervals. If necessary, 4 additional doses of 8 mg/kg of body weight can be given at 12 hour intervals. Another effective dose regimen consists of a continuous intravnous infusion of from 0.05 mg/kg/hr to 2.0 mg/kg/hr. Of course, other dosing schedules and amounts are possible.

One aspect of this invention is the treatment of persons with grey matter edema by concomitant administration of a compound of Formula I or its salts, and an anti-inflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R.

S. Bourke et. al. (R. S. Bourke, M. A. Daze and H. K. Kimelberg, Monograph of the International Glial Cell symposium, Leige, Bel. Aug. 29-31, 1977 and reference cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiologcal response primarily involving swelling of astroglial as a secondary, inhibitable process. At the molecular level, the sequence appears to be: trauma, elevation of extracellular $K^+$ and/or release of neurotransmitters, edema, and necrosis Astroglial swelling results directly from a $K^+$-dependent, cation-coupled, chloride transport from the extracellular into the intracellular compartment with a concomitant movement of an osmotic equivalent of water. Thus an agent that specifically blocks chloride transport in the astroglia is expected to block the edema caused by trauma and other insults to the brain. It is also important that such chloride transport inhibitors be free or relatively free of side effects, particularly those characteristics of many chloride, transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R. ; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K.; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, C.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V. ; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention are tested for activity. This test provides the principal in vitro evaluation and consists of a determination of concentration vs. response curve. The addition of $HCO_3^{31}$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-reponse curves are then obtained. The data are expressed as percent $HCO_3^-$-stimulated swelling vs. drug concentration, from which the concentration of drug providing 50% inhibition of $HCO_3^-$-stimulated swelling ($I_{50}$ in molarity) is interpolated.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims. All temperatures in the examples are in Centigrade unless otherwise indicated.

EXAMPLE 1

In Vitro Cerebrocortical Tissue Slice Assay

Adult cats of 2-3 kg body weight are employed in tissue slice studies. Prior to sacrifice, the animals are anesthetized with ketamine hydrochloride gassed for (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N2hydroxyethyl-piperazine-N'-2- ethanesulfonic acid, titrated with NaOH to pH 7.4), 20. Except when adding $HCO_3^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2$/97.5% $O_2$ instead of 100% $O_2$.

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO_3^-$-stimulated swelling that occurred in its presence, computed as a percent of the maximum possible. Tissue and media $Na^+$ and $K^+$ levels are determined by emission flame photometry with $Li^+$ internal standard; $Cl^-$ levels are determined by amperometric titration. Tissue viability during incubation is monitored by manometry.

EXAMPLE 2

R(+)
5,6-Dichloro-1,2,9,9a-tetrahydro-7-hydroxy-99-propyl-3H-flouren-3-one

R(+) (5,6-Dichloro-2,3,9,9a-tetrahydro-3-oxo-9a-propyl-1H-fluoren-7-yl)oxy]acetic acid (7.38 g, 20 mMole) was added to a stirring melt of pyridine hydrochloride (73.8 g, 630 mMole) at 190° C. and heated for 15 minutes. The mixture was quickly poured, with stirring, into crushed ice (400 g) and the resulting solid was separated by filtration, washed with $H_2O$, resuspended in $H_2O$, refiltered, thoroughly washed with $H_2O$ and dried. The yield of product was 6.4 g (100%); this product was purified by extraction with ethyl acetate via a Soxhlet, the solvent evaporated and the residue washed with ether to give material, mp 253°–255° C. $[\alpha]_D^{25}$ +177.4 (c=1 THF).

Analysis for $C_{16}H_{16}Cl_2O_2$: Calculated: C, 61.75; H, 5.18. Found: C, 61.96; H, 5.41.

EXAMPLE 3

R(+)
[(5,6-Dichloro-1,2,9,9a-tetrahydro-9a-propyl-1H-fluoren-7-vl)oxy]ethanol

R(+) 5,6-Dichloro-1,2,9,9a-tetrahydro-7-hydroxy-9a-propyl-3H-fluoren-3-one (3.3 g, 10.6 mMole), 2-iodoethanol (2.74 g, 15.9 mMole), potassium carbonate (2.19 g, 15.9 mMole) and acetone (500 ml) were stirred and refluxed for 24 hours. The mixture was filtered and the filtrate evaporated to dryness in vacuo. The residue was treated with water, the water layer removed and the residue dissolved in acetone. Evaporation of the acetone solution produced a residue which was chromatographed on a silica gel column. The material was placed on the column in a little acetonitrile and eluted with a butyl chloride-acetonitrile 7:3 mixture. Evaporation of the appropriate cuts gave 2.82 g of product, which after recrystallization from butyl chloride melted at 125°–127° C.

Analysis for $C_{18}H_{20}Cl_2O_3$: Calculated: C, 60.85; H, 5.67. Found: C, 61.10; H, 5.82.

EXAMPLE 4

R(+)[(5,6-Dichloro-1,2,9,9a-tetrahydro-9a-propyl-1H-fluoren- 7-yl)oxy]ethyl 4-(dimethylamino)butyrate hydrochloride 4-(Dimethylamino)butyric acid hydrochloride (603 mg, 3.36 mMole) and 1,5-diazabicylco [4.3.0]nonane (DBN) (447 mg, 3.36 mMole) in tetrahydrofuran (100 ml) were stirred under anhydrous conditions for 2 hours. Then, R(+) [(5,6-dichloro-1,2,9,9a-tetrahydro-9a-propyl-1H-fluoren-7-yl)oxy]ethanol was added and the mixture stirred for 16 hours.

The reaction mixture was evaporated in vacuo and the residue extracted with dichloromethane. The dichloromethane extract was washed with a brine solution and then with a 0.1 normal hydrochloric acid solution. The dichloromethane solution was dried over $MgSO_4$ and evaporated to dryness in vacuo. The residue was treated with boiling ethyl acetate which gave the solid product 1.03 g m.p. 146°–148°.

Analysis for $C_{24}H_{31}Cl_2NO_4 \cdot HCl$: Calculated: C, 57.09; H, 6.39; N, 2.77. Found: C, 56.81; H, 6.51; N, 2.74.

EXAMPLE 5

R(+)
[(5,6-Dichloro-1,2,9,9a-tetrahydro-9a-propyl-1H-fluoren-7-yl)oxy]ethyl (dimethylamino)acetate hydrochloride By conducting the reaction as described in Example 4 except that the 4-(dimethylamino)butyric acid hydrochloride was replaced by an equivalent amount of N,N-dimethylglycine, there was obtained R(+) [(5,6-dichloro-1,2,9,9a-tetrahydro-9a-propyl-1H-fluoren-7-yl)oxy]ethyl (dimethylamino)acetate hydrochloride.

EXAMPLE 6

R(+)
[(5,6-Dichloro-1,2,9,9a-tetrahydro-9a-propyl-1H-fluoren. 7-yl)oxy]ethyl 3-carboxypropionate Succinic acid (1.3 g, 11 mMole) in dimethylformamide (50 ml) was treated with imidazole sodium (991 mg, 11 mMole) and then carbonyldiimidazole (1.78 g, 11 mMole) added. After stirring for 20 minutes, [(5,6-dichloro-1,2,9,9a-tetrahydro-9a-propyl-1H-fluoren-7- yl)oxy]ethanol (3.55 g, 10 mMole) was added followed by sodium methoxide (27 mg) and the mixture stirred for 20 hours at ambient temperature.

The solvent was removed by evaporation at reduced pressure and the residue treated with water (20 ml). The mixture was extracted with dichloromethane and the water layer separated and acidified with hydrochloric acid. The mixture was extracted with dichloromethane and the extract dried over MgSO$_4$. Evaporation of the solvent gave the product.

EXAMPLE 7

(Z) R(+) [(5,6-Dichloro-1,2,9,9a-tetrahydro-9a-propyl-1H-fluoren-7-yl)oxy]ethyl3-carboxyacrylate By carrying out the reaction as described in Example 6 except that the succinic acid was replaced by an equimolar amount of maleic acid, there was obtained (Z) R (+) [(5,6-dichloro-1,2,9,9a-tetrahydro-9a-propyl-1H-fluoren- 7-yl)oxy]ethyl 3-carboxyacrylate.

EXAMPLE 8

Parenteral solution of R(+) [(5,6-Dichloro-1,2,9,9a-tetrahydro-9a-propyl -1H-fluoren- 7-yl)oxy]ethanyl4 4-(dimethylamino)butyrate hydrochloride The parenteral solution of R(+) [(5,6-dichloro-1,2,9,9a-tetrahydro-9a-propyl-1fluoren-7-yl)Oxy]ethanyl 4-(dimethylamino)butyrate hydrochloride (Example 4) (542 mg) is dissolved by stirring and warming with sufficient water to bring the total volume to 10 ml and the solution is sterilized by filtration. All the water that is used in the preparation is pyrogen-free. The concentration of the active ingredient (calculated as free base) in the final solution is 5%.

Similar parenteral solutions of the basic esters of this invention can be prepared by replacing the active ingredient of this Example by any of the other basic ester compounds of this invention.

EXAMPLE 9

Parenteral solution of the Sodium Salt R(+) [(5,6-Dichloro-1,2,9,9a-tetrahydro-9a-propyl-1-fluoren-7-yl)oxy]ethyl 3-carboxypropionate The parenteral solution of the Sodium Salt R(+) [(5,6-Dichloro-1,2,9,9a-tetrahydro-9a-propyl-1H-fluoren-7-yl)oxy]ethyl 3-carboxyproprionate (Example 6) (500 mg) is dssolved by warming with a solution of 0.25 N sodium bicarbonate (4.53 ml). The solution is diluted to 10 ml with water and sterilized by filtration. All the water used in the preparation is pyrogen-free. The concentration of the active ingredient (calculated as free acid) in the final solution is 5%.

Similar parenteral solutions of the acidic esters of the compounds of this invention can be prepared by replacing the active ingredient of this Example by any other acidicester compounds of this invention.

EXAMPLE 10

Dry-Filled Capsules Containing 100 mg of Active Ingredient Per Capsule

|  | Per Capsule |
| --- | --- |
| R(+) [(5,6-dichloro-1,2,9,9a-tetra-hydro-9a-propyl-1H—fluoren-7-yl)-oxy]ethyl 4-(dimethylamino)-butyrate hyrochloride | 108.4 mg |
| Lactose | 90.6 mg |
| Magnesium Stearate | 1 mg |
| Capsule (Size No. 1) | 200 mg |

The R(+) [(5,6-dichloro-1,2,9,9a-tetrahydro-9a-propyl-1H-fluoren-7-yl)oxy]ethyl 4-(dimethylamino)butyrate hydrochloride (Example 3) is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other compounds of this invention.

What is claimed is:

1. A compound of the formula:

(I)

RO—(CH$_2$)$_x$O—[fluorene ring system with R$^1$, X, Y, and =O]

wherein:

R is H, $-\overset{O}{\underset{\|}{C}}(CH_2)_yN(CH_3)_2$, $-\overset{O}{\underset{\|}{C}}-CH_2CH_2COOH$, $-\overset{O}{\underset{\|}{C}}-CH=CH_2COOH$;

R$^1$ is lower alkyl, branched or unbranched, containing from 1 to 5 carbon atoms, aryl, halo substituted aryl, aralkyl, cycloalkyl containing from 3 to 6 nuclear carbon atoms, or cycloalkyl-lower alkyl containing from 4 to 7 total carbon atoms;

X and Y are halo or lower alkyl;

x is 1 to 4; and y is 1 to 3.

2. A compound of the formula:

(II)

R$^2$O—(CH$_2$)$_x$O—[fluorene ring system with R$^3$, Cl, Cl, and =O]

wherein:

R$^2$ is hydrogen, $(CH_3)_2NCH_2\overset{O}{\underset{\|}{C}}-$, $(CH_3)_2NCH_2CH_2\overset{O}{\underset{\|}{C}}-$, $HOOCCH_2CH_2\overset{O}{\underset{\|}{C}}-$, and $HOOCCH=CH\overset{O}{\underset{\|}{C}}-$;

R$^3$ is lower alkyl, branched or unbranched, containing from 1 to 5 carbon atoms; and x is 1 or 2.

3. A compound of claim 1, which is R(+) [(5,6-dichloro-1,2,9,9a-tetrahydro-9a-propyl-1H-fluoren-7-yl)oxy]ethanol.

4. A compound of claim 1, which is R(+) [(5,6-dichloro-1,2,9,9a-tetrahydro-9a-propyl-1H-fluoren-7-yl)oxy]ethyl 4-(dimethylamino)butyrate hydrochloride.

5. A compound of claim 1, which is R(+) [(5,6-dichloro-1,2,9,9a-tetrahydro-9a-propyl-1H-fluoren-7-yl)oxy]ethyl (dimethylamino)acetate hydrochloride.

6. A compound of claim 1, which is R(+) [(5,6-dichloro-1,2,9,9a-tetrahydro-9a-propyl-1H-fluoren-7-yl)oxy]ethyl 3-carboxypropionate.

7. A compound of claim 1, which is (Z) R(+) [(5,6-dichloro-1,2,9,9a-tetrahydro-9a-propyl-1H-fluoren-7-yl)oxy]ethyl 3carboxyacrylate.

8. A pharmaceutical composition useful in the treatment of brain injury comprising a pharmaceutical carrier and an effective amount of a compound of claim 1.

9. A method of treating a person with brain injury which comprises administering to such a person an effective amount of a compound of claim 1.

* * * * *